(12) United States Patent
Lee

(10) Patent No.: US 11,857,311 B2
(45) Date of Patent: Jan. 2, 2024

(54) MULTI-PURPOSE VIDEO MONITORING CAMERA

(71) Applicant: Prime Dragon Limited, Kowloon (HK)

(72) Inventor: Wai Hung Lee, Kennedy Town (HK)

( * ) Notice: Subject to any disclaimer, the term of this patent is extended or adjusted under 35 U.S.C. 154(b) by 926 days.

(21) Appl. No.: 16/820,747

(22) Filed: Mar. 17, 2020

(65) Prior Publication Data

US 2021/0290105 A1 Sep. 23, 2021

(51) Int. Cl.

| A61B 5/113 | (2006.01) |
|---|---|
| H04N 5/33 | (2023.01) |
| A61B 5/01 | (2006.01) |
| A61B 5/11 | (2006.01) |
| A61B 5/1171 | (2016.01) |
| H04N 23/611 | (2023.01) |

(52) U.S. Cl.
CPC ............ *A61B 5/113* (2013.01); *A61B 5/01* (2013.01); *A61B 5/1114* (2013.01); *A61B 5/1128* (2013.01); *A61B 5/1176* (2013.01); *H04N 5/33* (2013.01); *H04N 23/611* (2023.01)

(58) Field of Classification Search
CPC ......... A61B 5/113; A61B 5/01; A61B 5/1114; A61B 5/1128; A61B 5/1176; H04N 5/33; H04N 23/611; H04N 23/11; H04N 7/18
See application file for complete search history.

(56) References Cited

U.S. PATENT DOCUMENTS

| 2007/0276270 | A1* | 11/2007 | Tran | A61B 5/0022 600/508 |
|---|---|---|---|---|
| 2009/0003708 | A1* | 1/2009 | Steinberg | H04N 23/80 382/190 |
| 2016/0171922 | A1* | 6/2016 | Lee | G09G 3/344 345/545 |
| 2020/0291919 | A1* | 9/2020 | Loh | H02K 7/183 |
| 2021/0290105 | A1* | 9/2021 | Lee | A61B 5/1176 |
| 2021/0297628 | A1* | 9/2021 | Lee | H04N 7/18 |

FOREIGN PATENT DOCUMENTS

| CN | 109276384 | A | * | 1/2019 | ............... A61B 5/00 |
|---|---|---|---|---|---|
| CN | 110101392 | A | * | 8/2019 | ............... A61B 3/11 |
| CN | 110365947 | A | * | 10/2019 | ........... A61B 5/0059 |
| EP | 2980548 | A1 | * | 2/2016 | ........... A61B 5/0008 |

* cited by examiner

*Primary Examiner* — Sean P Dougherty

(57) ABSTRACT

The multi-purpose video monitoring camera includes a microprocessor, a CMOS video camera, a thermographic video camera, a display unit and a mic array. The microprocessor includes a baby presence detection module, a warning module, a motion detection module, a breathing detection module, a hot air exhalation detection module, a chest movement detection module, a breathing sound detection module, a suffocation detection module, a temperature measurement module, a urination and defecation detection module, an air conditioning module and a baby growth rate module. By using inputs from both the CMOS video camera and the thermographic video camera, the accuracy of the baby presence detection module is improved.

19 Claims, 2 Drawing Sheets

MULTI-PURPOSE VIDEO MONITORING CAMERA

BACKGROUND OF THE INVENTION

The present invention relates to a video monitoring camera and more specifically relates to a multi-purpose video monitoring camera.

In most video monitoring camera, especially in video baby monitors, video analytic or artificial intelligence are used to help detect a baby's breathing, movement/motion, and sleep pattern and so forth. However, the accuracy of such cameras is not satisfactory. For example, in one of our research for sleep analytic of a baby via motion detection, it is necessary to detect the presence of a baby by detecting the baby head first (i.e. head detection). However, in most cases the detection algorithm is to detect a ball shape face or head first. There are a lot of false triggers if there is a doll in the crib or if the bed sheet got some ball shape pattern. The video analytic algorithm will mistakenly identify the doll head or ball shape objects as baby head, and resulting in a wrong assumption that there is a baby in the crib.

It is possible to improve head detection by adjusting the sensitivity of the head detection algorithm. However, it is very difficult to find the best balance point. If sensitivity is too high, it is easy to conclude that the baby is in the crib (false positive happens). In other words, even if the baby is not in the crib, but the baby monitor mistakenly judges that a baby is in the crib without movement and thus interprets that the baby is sleeping in the crib. Wrong information is therefore provided to users. In contrast, if the sensitivity is too low, false negative will happen. In other words, even if the baby is the crib, the baby monitor wrongly judges that the baby is not there, and thus even if the baby moved, the baby monitor will ignore such movement and report that there is no baby in the crib. Either way, it is not possible to give accurate sleep analytic to parents.

BRIEF SUMMARY OF THE INVENTION

In view of the aforesaid disadvantages now present in the prior art, it is an object of the present invention to provide a multi-purpose video monitoring camera with improved accuracy.

To attain this, the multi-purpose video monitoring camera comprises a microprocessor; a CMOS video camera operably coupled to the microprocessor; a thermographic video camera operably coupled to the microprocessor and aligned with the CMOS video camera so that the thermographic video camera and the CMOS video camera have overlapping fields of view; and a display unit operably coupled to the microprocessor.

The microprocessor comprises a breathing detection module for calculating a breathing rate of a baby, and a suffocation detection module which is activated after the breathing rate of the baby determined by the breathing detection module falls below a predetermined threshold; the suffocation detection module is configured to: (1) obtain input from the CMOS video camera and the thermographic video camera; (2) detect position of head of the baby in the field of view of the thermographic video camera and perform face recognition on the input obtained in (1) to determine if forehead of the baby is present in the field of view of the CMOS video camera; (3) if output from (2) indicates that forehead of the baby is not present, control a warning module of the microprocessor to output a warning signal; (4) if output from (2) indicates that forehead of the baby is present, perform face recognition on the input obtained in (1) to determine if nose and mouth of the baby is present in the field of view of the CMOS video camera; (5) if output from (4) indicates that nose and/or mouth of the baby is not present, control the warning module to output a warning signal.

The suffocation detection module reduces the false alarm by further configuring to: (6) if output from (4) indicates that nose and/or mouth of the baby is not present, determine head position of the baby from the input obtained in (1), measure head length and head width of the baby, and determine if a ratio of the head length to the head width deviates from a predetermined ratio; (7) if output from (6) indicates that the ratio of the head length to the head width deviates from a predetermined ratio, control the warning module to output a warning signal.

The microprocessor further comprises a motion detection module which is configured to determine whether the baby is idle without significant movement for a predetermined period of time, and one of more of a hot air exhalation module, a chest movement module and a breathing sound detection module; the breathing detection module is configured to calculate the breathing rate of the baby based on outputs from one or more of the hot air exhalation module, the chest movement module and the breathing sound detection module if the motion detection module determines that the baby is idle without significant movement for a predetermined period of time.

The hot air exhalation detection module is configured to: (1) obtain position of head of the baby in the fields of view of the CMOS video camera and the thermographic video camera; (2) detect position of nose and mouth of the baby in the fields of view of the CMOS video camera and the thermographic video camera from the position of head of the baby obtained in (1); (3) detect temperature variation pattern in the position of nose and mouth of the baby in the fields of view of the thermographic video camera detected in (2); (4) calculate a first breathing rate of the baby based on output obtained in (3).

The chest movement detection module is configured to: (1) obtain positions of head and limbs of the baby in the fields of view of the CMOS video camera and the thermographic video camera; (2) estimate position of chest based on positions of head and limbs of the baby obtained in (1); (3) detect pixel-wise spatial variation of the position of chest from frame to frame and convert the spatial variation into frequency domain; (4) determine the largest magnitude in the frequency domain; (5) calculate a second breathing rate of the baby based on output obtained in (4).

The multi-purpose video monitoring camera further comprises a mic array operably coupled to the microprocessor; the breathing sound detection module is configured to: (1) obtain input from the mic array; (2) perform beamforming on the input obtained in (1) to focus on sound produced near mouth and nose of the baby; (3) detect sound pressure level of output from (2); (4) build a history of the sound pressure level detected in (3); (5) calculate a third breathing rate of the baby by counting number of cycles per minute between sound pressure level higher than a predetermined threshold value and sound pressure level lower than a predetermined threshold value from the history of sound pressure level in (4).

The breathing detection module is configured to determine the breathing rate of the baby by comparing the first breathing rate obtained from the hot air exhalation detection module, the second breathing rate obtained from the chest movement detection module and the third breathing rate obtained from the breathing sound detection module and selecting a maximum amongst the first, second and third breathing rates.

The microprocessor further comprises a baby presence detection module which is configured to: (1) obtain input from the CMOS video camera; (2) perform face recognition on the input obtained in (1) to determine if a baby is present in the field of view of the CMOS video camera; (3) if it is determined from (2) that a baby is present in the field of view of the CMOS video camera, confirm baby presence; (4) if it is determined from (2) that a baby is not present in the field of view of the CMOS video camera, obtain input from the thermographic video camera to identify a human head region in the field of view of the thermographic video camera; (5) perform face recognition on the input obtained in (1) at a region corresponding to the human head region in the field of view of the thermographic video camera to determine if a baby is present in the field of view of the CMOS video camera; (6) if it is determined from (5) that a baby is present in the field of view of the CMOS video camera, confirm baby presence; (7) if it is determined from (5) that a baby is not present in the field of view of the CMOS video camera, confirm baby absence; (8) if baby presence is confirmed, update check-in/check-out status as check-in; (9) if baby absence is confirmed, update check-in/check-out status as check-out.

The motion detection module is activated after the baby presence detection module updates check-in/check-out status as check-in and is configured to: (1) obtain input from the CMOS video camera and the thermographic video camera; (2) detect positions of head and limbs of the baby in the fields of view of the CMOS video camera and the thermographic video camera from the input obtained in (1); (3) determine posture of the baby by measuring height levels of the detected head and limbs, curvature and orientation of the detected limbs, and separation among the detected head and limbs; (4) determine motion of the baby based on frame by frame analysis of the posture determined in (3) over a period of time; (5) build a history of the motion determined in (4); (6) determine whether the baby is idle without significant movement for a predetermined period of time from the history built in (5).

The warning signals output from the warning module of the microprocessor are in form of warning messages displayed on the display unit; the multi-purpose video monitoring camera is wirelessly connected to an external mobile device which is installed with an app for receiving and outputting the warning messages output from the microprocessor.

The microprocessor further comprises a temperature measurement module configured to: (1) determine a body temperature of the baby by selecting the highest temperature in the field of view of the thermographic video camera; (2) build a history of the body temperature obtained in (1); (3) control the warning module to output a warning signal if the body temperature in the history exceeds a predetermined level longer than a predetermined period of time.

The multi-purpose video monitoring camera further comprises a thermistor for calibrating input of the thermographic video camera by compensating difference between ambient temperature and operation temperature of the multi-purpose video monitoring camera.

The microprocessor further comprises a urination and defecation detection module configured to: (1) obtain positions of legs of the baby in the fields of view of the CMOS video camera and the thermographic video camera; (2) estimate position of diaper based on positions of legs of the baby obtained in (1); (3) detect and build a history of temperature at the position of diaper estimated in (2); (4) control the warning module to output a warning signal if the temperature in the history built in (3) indicates a rapid increase follows by a gradual decrease.

The multi-purpose video monitoring camera further comprises an IR transmitter operably coupled to the microprocessor; the microprocessor further comprises an air conditioning module configured to: (1) measure ambient temperature near the baby in the fields of view of the CMOS video camera and the thermographic video camera; (2) control the IR transmitter to send control signal to an air conditioner to adjust control temperature of the air conditioner if the ambient temperature measured in (1) exceeds or falls below a predetermined range.

The multi-purpose video monitoring camera further comprises a proximity sensor operably coupled to the microprocessor; the microprocessor further comprises a baby growth rate module configured to: (1) obtain positions of head and limbs of the baby in the field of view of the CMOS video camera from the motion detection module; (2) determine a baby length by measuring distance between top of head to toes if the posture determined by the motion detection module is a straight posture; (3) calculate actual baby length based on the baby length determined in (2) and a scale factor which is based on either dimension of object nearby the baby, manual measurement of the actual baby length in regular basis, or proximity distance between the baby and the multi-purpose video monitoring camera; (4) build a history of the actual baby length calculated in (3).

The baby growth rate module is further configured to: (3.1) perform object recognition on input obtained from the CMOS camera to identify an object positioned near the baby; (3.2) measure dimension of the object identified in (3.1); (3.3) recall actual dimension of the object identified in (3.2) from a database which stores actual dimensions of objects; (3.4) calculate actual baby length based on the baby length determined in (2), the dimension measured in (3.2) and the actual dimension recalled in (3.3).

The multi-purpose video monitoring camera further comprises a rotate-pan-tilt mount operably coupled to the microprocessor and controlled by the microprocessor to adjust the CMOS video camera and the thermographic video camera such that the baby is always in center of the fields of view of the CMOS video camera and the thermographic video camera.

The CMOS video camera is a low lux CMOS video camera. The thermographic video camera has a resolution of 32×32 pixels which can measure human body temperature with an accuracy of up to ±0.2° C. at a distance of 1.5 meters from a human body.

DETAILED DESCRIPTION OF THE INVENTION

Figure 1:
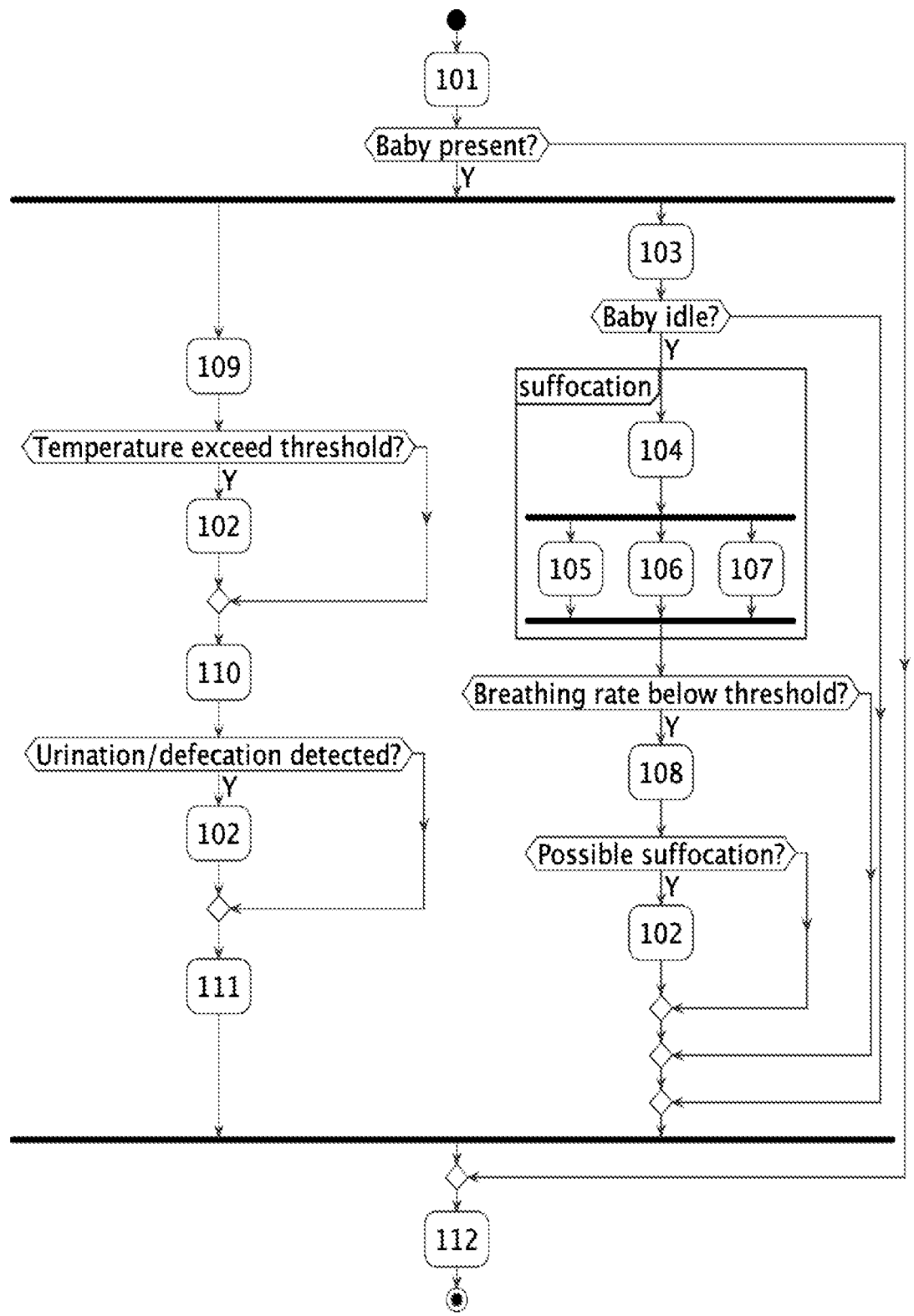
FIG. 1 is a schematic diagram of a preferred embodiment of the present invention.
Figure 2:
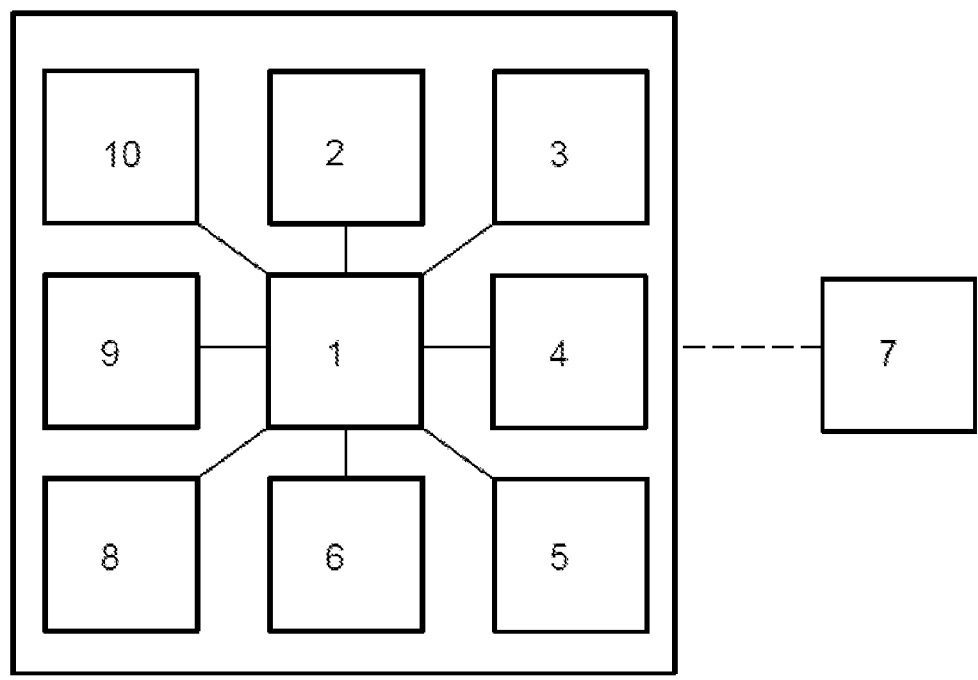
FIG. 2 is a flow chart illustrating the operation processes of a preferred embodiment of the present invention.

FIGS. 1 to 2 illustrate a preferred embodiment of the multi-purpose video monitoring camera of the present invention, which comprises a microprocessor 1, a CMOS video camera 2, a thermographic video camera 3, a display unit 4 and a mic array 5. The CMOS video camera 2 is a low lux CMOS video camera operably coupled to the microprocessor 1. The thermographic video camera 3 is operably coupled to the microprocessor 1 and aligned with the CMOS video camera 2 so that the thermographic video camera 3 and the CMOS video camera 2 have overlapping fields of view. More specifically, the CMOS video camera 2 and the thermographic video camera 3 are calibrated to have the same point of view in any rotational position. In other words, the center point of video data and thermographic data is equal. In this embodiment, the thermographic video camera 3 has a resolution of 32×32 pixels which can measure human body temperature with an accuracy of up to ±0.2° C. at a distance of 1.5 meters from a human body. The display unit 4 is operably coupled to the microprocessor 1. The mic array 5 is operably coupled to the microprocessor 1.

The multi-purpose video monitoring camera is fixedly mounted next to a crib where a baby sleeps. In this embodiment, the multi-purpose video monitoring camera further comprises a rotate-pan-tilt mount 6 operably coupled to the microprocessor 1 and controlled by the microprocessor 1 to adjust the CMOS video camera 2 and the thermographic video camera 3 such that the baby in the crib is always in center of the fields of view of the CMOS video camera 2 and the thermographic video camera 3.

The microprocessor 1 comprises a baby presence detection module 101, a warning module 102, a motion detection module 103, a breathing detection module 104, a hot air exhalation detection module 105, a chest movement detection module 106, a breathing sound detection module 107, a suffocation detection module 108, a temperature measurement module 109, a urination and defecation detection module 110, an air conditioning module 111 and a baby growth rate module 112.

The baby presence detection module 101 is configured to:
(1) obtain input from the CMOS video camera 2;
(2) perform face recognition on the input obtained in (1) to determine if a baby is present in the field of view of the CMOS video camera 2;
(3) if it is determined from (2) that a baby is present in the field of view of the CMOS video camera 2, confirm baby presence;
(4) if it is determined from (2) that a baby is not present in the field of view of the CMOS video camera 2, obtain input from the thermographic video camera 3 to identify a human head region in the field of view of the thermographic video camera 3;
(5) perform face recognition on the input obtained in (1) at a region corresponding to the human head region in the field of view of the thermographic video camera 3 to determine if a baby is present in the field of view of the CMOS video camera 2;
(6) if it is determined from (5) that a baby is present in the field of view of the CMOS video camera 2, confirm baby presence;
(7) if it is determined from (5) that a baby is not present in the field of view of the CMOS video camera 2, confirm baby absence;
(8) if baby presence is confirmed, update check-in/check-out status as check-in;
(9) if baby absence is confirmed, update check-in/check-out status as check-out.

In operation, when the parent or helper is carrying the baby close to the crib and put the baby into the crib, the head of the baby should be visible to both the CMOS video camera 2 and the thermographic video camera 3, and thus the baby presence detection module 101 should be able to confirm baby presence and update check-in/check-out status as check-in. The check-in process starts the monitoring on the baby. If the parent or helper may remember to bring the baby to the area in front of the CMOS video camera 2 and the thermographic video camera 3, the check-in process can be more secured. Also, a higher resolution snapshot of the baby head including cloth, hat, or other objects can be recognized and used in later stage to monitor the movement of baby. Of course, from baby caring point of view, it is not recommended for baby to wear more things on the head. Thus, in most cases, the baby head is in clearance without any cover. Similarly, when an adult is coming to the crib and taking away the baby from the crib for other activity such as meal time or play time, the baby presence detection module 101 should be able to confirm baby absence and update check-in/check-out status as check-out. At this time, the face of the parent or helper may also be visible to the CMOS video camera 2. Face recognition can be applied to the adult who takes the baby away from crib. The person and time record can be recorded and parent is able to check who is the last person to carry the baby and when the baby leaves the crib. Moreover, the baby presence detection module 101 may also detect that the baby is moving up into the air, which is not possible for the baby to do by himself/herself. This is a clear signal for check-out process when the baby is not under monitoring anymore.

Using the check-in and check-out mechanism, the presence of baby in the crib is definitely confirmed without any false trigger on baby activity when baby is not in the crib. In contrast, after the check-in process, the baby should be visible in the fields of view of the CMOS video camera 2 and the thermographic video camera 3 without any exception since the baby is not possible to leave the crib by himself/herself. Therefore, by means of the rotate-pan-tilt mount 6, the CMOS video camera 2 and the thermographic video camera 3 may change and enlarge the monitoring area to search the baby if the monitoring area cannot cover the whole crib. In other words, the CMOS video camera 2 and the thermographic video camera 3 should follow the baby movement and make the center of monitoring area around the baby. If the baby is not detected between check-in and checkout mechanism, the baby may be covered by blanket, toy or other things in the crib. In this situation, the parent should be warned unless baby movement is indirectly confirmed by checking the movement of object which covered the baby. For example, if the baby is playing inside the blanket, the baby movement may couple to the blanket. It is possible to confirm baby presence since the blanket movement can be detected by the CMOS video camera 2.

Apart from detecting baby presence by the CMOS video camera 2, there is a second level of baby presence detection by the thermographic video camera 3. The thermographic video camera 3 captures every position in the crib and creates a heat zone image in crib region. Then, the region will be filtered by the temperature ranging from 34-37 degree Celsius. Due to the heat radiation from the baby, the filtered area of heat zone image may be the location of baby head or limbs. Normally, the crib is placed in the room where the ambient temperature is not higher than 30 degree Celsius. So, the filtered area by using heat zone image should be accurate. If the thermographic video camera 3 has higher resolution, it is even possible to obtain a head contour due to the blood circulation in forehead. Then, this thermal fingerprint can be used to recognize the head. Once the potential location of baby head is identified, the CMOS video camera 2 can be used to do face recognition on the area identified by the thermographic video camera 3. If the check-in mechanism is somehow failed due to unknown reason, this second level will trigger monitoring process on the baby automatically when baby presence is detected. Using these two levels, the accuracy of presence detection is secured.

The warning module 102 is configured to output warning signals; the warning signals output from the microprocessor 1 are in form of warning messages displayed on the display unit 4. The multi-purpose video monitoring camera is wirelessly connected to an external mobile device 7 which is installed with an app for receiving and outputting the warning messages output from the microprocessor 1.

The motion detection module 103 is activated after the baby presence detection module 101 updates check-in/check-out status as check-in and is configured to:
(1) obtain input from the CMOS video camera 2 and the thermographic video camera 3;
(2) detect positions of head and limbs of the baby in the fields of view of the CMOS video camera 2 and the thermographic video camera 3 from the input obtained in (1);
(3) determine posture of the baby by measuring height levels of the detected head and limbs, curvature and orientation of the detected limbs, and separation among the detected head and limbs;
(4) determine motion of the baby based on frame by frame analysis of the posture determined in (3) over a period of time;
(5) build a history of the motion determined in (4);
(6) determine whether the baby is idle without significant movement for a predetermined period of time from the history built in (5).

In operation, after the baby presence detection module 101 updates check-in/check-out status as check-in, the monitoring with the CMOS video camera 2 and the thermographic video camera 3 is continuous. Apart from baby head, the heat radiation of two arms and two legs are other baby parts which are clearly visible in thermographic image within body temperature range. Using the movement of head, arm and legs, the baby motion can be recognized. For example, when the baby is standing, head is coming to higher position, two limbs with larger separation will be middle and another two limbs with smaller separation will be lower in position; when the baby is crawling, four limbs will have similar height position while two of them are curved with knees touching down. By measuring the height levels of different body parts, curvature and orientation of limbs, as well as separation among head, arms and legs, the motion detection module 103 can determine the posture of the baby. Using frame by frame transition tracking, the motion is detected. Similarly, head, arms and legs can be recognized in the CMOS video camera 2 too. Then, motion detection through the CMOS video camera 2 will provide another level of confirmation on the baby motion. This second level is useful when the resolution of the thermographic video camera 3 is low.

The motion detection module 103 allows understanding of the activities of the baby in the crib and clearly identifies the period when the baby is idle without significant movement. In the period when the baby is idle, it is possible for the baby to have nap or suck a doll/pacifier. Then, the image changes either in the CMOS video camera 2 or the thermographic video camera 3 is very small compared frame to frame. From monitoring point of view, it poses a challenge to identify whether the baby is safe or not. So, additional processing should be done.

By having the motion detection module 103 to build a history of the motion of the baby, it would then be possible to generate the activity pattern or favorite behavior of the baby when the baby is alone in the crib. The baby may do certain activities in sequence or based on the length of time when the baby is alone. Each baby is different but somehow there is a trend or track record to follow. If the motion detected by the motion detection module 103 deviates from the history a lot, some issues may happen.

Secondly, based on the history built by the motion detection module 103, an indicator of activity energy level can be calculated based on the amount of certain activities the baby performed. Some activities need more energy than others to do. So, the transition of activity energy should be reasonable. For example, it requires so much energy for the baby pushing around on its stomach. So, the duration may not be too long. If the detection is longer than normal with an idle position follow-up, certain attention should be acted to cross check other indicator to see if the alert is needed to generate.

Thirdly, the posture of idle position is correlated to the previous motion the baby performed. When the baby transits from sitting to lying, it is highly possible for the baby to lie on its back. When the baby transits from pushing around on stomach to lying, it is highly possible for the baby to lie on its stomach. With the history built by the motion detection module 103, the aforementioned posture information could also be used to analyze if the baby is idle without significant movement for a predetermined period of time.

When the baby is idle without significant movement for a predetermined period of time, other detection in the following sections will be activated to further identify the baby situation and generate alert to parent when it is determined that the baby may be in danger.

The breathing detection module 104 calculates the breathing rate of the baby based on outputs from the hot air exhalation detection module 105, the chest movement detection module 106 and the breathing sound detection module 107 if the motion detection module 103 determines that the baby is idle without significant movement for a predetermined period of time.

The hot air exhalation detection module 105 is configured to:
(1) obtain the position of head of the baby in the fields of view of the CMOS video camera 2 and the thermographic video camera 3 from the motion detection module 103;
(2) detect position of nose and mouth of the baby in the fields of view of the CMOS video camera 2 and the thermographic video camera 3 from the position of head of the baby obtained in (1);
(3) detect temperature variation pattern in the position of nose and mouth of the baby in the fields of view of the thermographic video camera 3 detected in (2);
(4) calculate a first breathing rate of the baby based on output obtained in (3).

In operation, when the baby is idle because of lying, sleeping or sucking a doll/pacifier, there is some hot air exhaled from the mouth or nose if the baby is breathing. The temperature of hot air exhaled is close to the body temperature. In air conditioning environment, the ambient air temperature is 25 degree Celsius which is much lower than the human body temperature. The exhaled air from the baby may be lower than 37 degree Celsius but it is still higher than the room temperature. With the high resolution of the thermographic video camera 3, the exhaled air is clearly seen as a temperature changing pattern near the nose or mouth. The pattern is very special since the area will increase from room temperature to a certain temperature close to baby body temperature in a short time. Then, the temperature will decrease naturally. The affected area of heat zone due to hot air exhalation is maintained constant as long as there is no movement for the baby. The variation of temperature in the area near the nose and mouth will form a cyclic pattern. By measuring the number of cycle or the frequency of the periodic signal, the first breathing rate of the baby could be obtained.

The chest movement detection module 106 is configured to:
(1) obtain positions of head and limbs of the baby in the fields of view of the CMOS video camera 2 and the thermographic video camera 3 from the motion detection module 103;
(2) estimate position of chest based on positions of head and limbs of the baby obtained in (1);
(3) detect pixel-wise spatial variation of the position of chest from frame to frame and convert the spatial variation into frequency domain;
(4) determine the largest magnitude in the frequency domain;
(5) calculate a second breathing rate of the baby based on output obtained in (4).

In operation, when the baby is idle, there is still some slightly movement. When the baby is breathing, the chest volume increases and decreases periodically. In the motion detection module 103, the head, arms and legs are already identified. Using triangularly among these visible body parts, the chest area is estimated. This area of interest from both the CMOS video camera 2 and the thermographic video camera 3 will feed into a special algorithm in order to detect the breathing rate. The algorithm can be Eulerian Video Magnification or other method to recognize the subtle movement under an almost still video streaming from the CMOS video camera 2 and the thermographic video camera 3. When the area of interest is focused on the chest area, the major component of subtle movement is caused by breathing. The subtle movement of object on top of chest will be analyzed to extract subtle movement due to increase and decrease of chest volume. The object on top of chest may experience up/down or left/right movement depending on the facing direction of baby face. The pixel-wise spatial changes of the area of interest around the chest area from frame to frame will be converted into frequency domain. The largest magnitude in frequency domain is mainly caused by the breathing frequency. Therefore, the corresponding frequency of breathing rate is significant in the frequency domain of the result of these algorithms, and the breathing rate is calculated from this frequency.

In most cases, the baby chest is not visible since the baby body is covered by cloth or blanket. The detection of chest movement is still possible. In most cases, the covered cloth and blanket has some weight and lay on the chest. When the baby is breathing in, the chest movement will push the cover material up. When the baby is breathing out, the chest volume reduces and the covered material will go down too due to the weight. Thus, the chest movement will couple to those covered material. This indirect detection on the covered material over the chest area will imply the same movement of chest. Then, the breathing rate can be calculated according in the previous description.

The breathing sound detection module 107 is configured to:
(1) obtain input from the mic array 5;
(2) perform beamforming on the input obtained in (1) to focus on sound produced near mouth and nose of the baby;
(3) detect sound pressure level of output from (2);
(4) build a history of the sound pressure level detected in (3);
(5) calculate a third breathing rate of the baby by counting number of cycles per minute between sound pressure level higher than a predetermined threshold value and sound pressure level lower than a predetermined threshold value from the history of sound pressure level in (4).

In operation, the breathing sound detection module 107 offers a third level of breathing detection. Wheezing is a high-pitched whistling sound made while the baby breathes. It's heard most clearly in exhalation, but in some cases, it can be heard when baby inhales. It's caused by narrowed airways. Using the mic array 5 consisting of 4 mic components or even more, it is possible to create beamforming on audio reception in order to focus on the sound produced near to baby mouth and nose. Baby breathing sound may be whistling, snoring, stridor or grunting. Also, irregular breathing pattern can be generated. The detection algorithm needs to use sound pressure level and silent period instead of audio characteristics to detect the breathing rate. In this embodiment, the threshold is dynamically adjusted so that it is 30% higher than the level in silent period. The threshold selection is to eliminate the variation among breathing sound patterns due to the conditions of nose, mouth and lung.

The breathing detection module 104 is configured to determine the breathing rate of the baby by comparing the first breathing rate obtained from the hot air exhalation detection module 105, the second breathing rate obtained from the chest movement detection module 106 and the third breathing rate obtained from the breathing sound detection module 107 and selecting a maximum amongst the first, second and third breathing rates.

The suffocation detection module 108 is activated after the breathing rate of the baby determined by the breathing detection module 104 falls below a predetermined threshold and is configured to:
(1) obtain input from the CMOS video camera 2 and the thermographic video camera 3;
(2) detect position of head of the baby in the field of view of the thermographic video camera 3 and perform face recognition on the input obtained in (1) to determine if forehead of the baby is present in the field of view of the CMOS video camera 2;
(3) if output from (2) indicates that forehead of the baby is not present, control the warning module 102 to output a warning signal;
(4) if output from (2) indicates that forehead of the baby is present, perform face recognition on the input obtained in (1) to determine if nose and mouth of the baby is present in the field of view of the CMOS video camera 2;
(5) if output from (4) indicates that nose and/or mouth of the baby is not present, determine head position of the baby from the input obtained in (1), measure head length and head width of the baby, and determine if a ratio of the head length to the head width deviates from a predetermined ratio;
(6) if output from (5) indicates that the ratio of the head length to the head width deviates from a predetermined ratio, control the warning module 102 to output a warning signal.

In operation, it should be possible to estimate the breathing rate of the baby in all possible circumstance by the hot air exhalation detection module 105, chest movement detection module 106 and the breathing sound detection module 107. The breathing rate can be as low as 20 times per minute during sleep but it will not reduce to zero. If zero breathing rate is detected for more than 10 seconds, there is a high chance that the baby has suffocation. There are two common situations for the baby to have suffocation. The first one is caused by the object blockage to baby's nose and mouth. Another one is because baby is sleeping on its stomach.

When the forehead of baby is visible to the present invention without any breathing rate detected, the face recognition and facial feature extraction is applied on the video data to identify the location of nose and mouth. If the extraction is successfully, there is little or no chance for baby's nose and mouth to be covered by object. Otherwise, the normal video data cannot recognize the mouth and nose or cannot recognize mouth and nose being covered. Then, additional processing should be applied to compensate the fault of face recognition due to visibility of partial face or other reason. There are two approaches of additional processing.

Firstly, the thermographic video camera 3 can determine which part of baby head is visible in the heat zone image. If the baby is sleeping sideway, left face or right face can be captured by the thermographic video camera 3. The curvature of head skull in the heat zone image will indicate if the whole head is exposed to the air or part of the head is covered by object such as blanket or cloth. When the nose and mouth is covered by object, the temperature of that area drops significantly. Thus, the head region with body temperature will not form a complete head skull curvature since the temperature of lower region for nose and mouth covered by object will drop significantly.

Secondly, the activity history constructed by the motion detection module 103 will estimate the length, width and orientation of head. The length is defined from cheek to the top of head while the width is the dimension measurement perpendicular to the length. When the nose and mouth is not covered by object, the aspect ratio between length and width will maintain similar. Otherwise, the length is much shorter. Based on the monitoring history, the aspect ratio range is calculated between length and width. When there is a suspicious situation for suffocation, the estimated length will compare to the actual measured length of the head. If the estimated length is shorter, it has high possibility that the nose and mouth is covered by object.

There is another reason to cause suffocation when the baby is sleeping on its stomach. In this situation, the forehead is fully facing down. In other words, the whole face is covered by mattress. In this situation, the face recognition fails since there is no facial feature visible. The thermographic video camera 3 will pick up the curvature of full head skull but the maximum temperature of the head region is 2 degree Celsius lower than the historical forehead temperature.

In either way, when the mouth and nose is covered by object or the baby is lying on its stomach, the parent should be warned to take some precaution action in order to prevent further suffocation in baby. In 2017, there were about 1,400 deaths due to SIDS, about 1,300 deaths due to unknown causes, and about 900 deaths due to accidental suffocation and strangulation in bed. Thus, the alert feature in the present invention is very important to keep baby safe.

The temperature measurement module 109 is configured to:
(1) determine a body temperature of the baby by selecting the highest temperature in the field of view of the thermographic video camera;
(2) build a history of the body temperature obtained in (1);
(3) control the warning module to output a warning signal if the body temperature in the history exceeds a predetermined level longer than a predetermined period of time.

In operation, the temperature measurement module 109 is activated whenever the baby forehead is visible to the thermographic video camera 3 so that the baby body temperature can be measured. The measured body temperature is recorded to the history of the body temperature for parent or medical person to review. If the baby is in any medical treatment, the temperature history is a useful information for understanding the effect of medicine to baby.

Normally, when the forehead is visible in the monitoring area, temperature of the area under monitoring will be captured; maximum temperature will be reported to local screen of the device and reported to system for record. The maximum temperature usually came from the two sides of the forehead where blood flows through the blood vessels. In babies and children, the average body temperature ranges from 97.9° F. (36.6° C.) to 99° F. (37.2° C.). Among adults, the average body temperature ranges from 97° F. (36.1° C.) to 99° F. (37.2° C.). In older adults over age 65, the average body temperature is lower than 98.6° F. (36.2° C.).

In order to further improve the measurement accuracy of temperature, a thermistor 8 is provided for calibrating input of the thermographic video camera 3 by compensating difference between ambient temperature and operation temperature of the multi-purpose video monitoring camera.

The temperature measurement module 109 will measure the body temperature continuously and keep them in history for later review. At the same, the temperature variation during a day and record at the similar time period among several days will be analyzed to see if the baby gets fever. In general, the baby body temperature is in the range from 97.9° F. (36.6° C.) to 99° F. (37.2° C.). For some reasons the baby will get higher than the aforementioned range while the baby is not fever, for example, if the baby is wrapped up tightly in a blanket, or the baby is in a very warm room, or the baby is very active, or the baby is cuddling a hot water bottle, or the baby is wearing a lot of clothes, or the baby is just having a bath, etc. In some cases, the body temperature will return to normal range after some time. In some other cases, the body temperature will maintain at a higher than normal range. Therefore, the present invention has a grace period for the high body temperature. In other words, if the temperature measurement module 109 detects that the body temperature in the history for only a short period of time, it would not control the warning module 102 to output a warning signal; but if the temperature measurement module 109 detects that the body temperature in the history exceeds a predetermined level longer than a predetermined period of time, it will control the warning module 102 to output a warning signal to alert the parent that either the baby really gets fever or the baby is wearing too much clothes in a very warm room. In both cases, parent should take some precaution in order to comfort the baby.

The urination and defecation detection module 110 is configured to:
(1) obtain positions of legs of the baby in the fields of view of the CMOS video camera and the thermographic video camera from the motion detection module;
(2) estimate position of diaper based on positions of legs of the baby obtained in (1);
(3) detect and build a history of temperature at the position of diaper estimated in (2);

(4) control the warning module to output a warning signal if the temperature in the history built in (3) indicates a rapid increase follows by a gradual decrease.

In operation, if the baby urinates and defecates, the diaper temperature will go up suddenly and gradually reduce. They will suggest that the baby urinates or defecates, and the urination and defecation detection module 110 can give alert to parents for diaper change.

The diaper has different temperature in dry and wet state. In dry state, the diaper is a good thermal isolation and the body temperature is not visible in the diaper area. However, when it is wet due to baby urination and defecation, the diaper temperature will increase since the temperature of urine or wet defecation is closed to the body temperature. Thus, the temperature of diaper will increase from room temperature to body temperature when it is full. The location of diaper in dry state is a relative location compared to the location of head and legs. Depending on the baby posture, the location of diaper can be triangularly identified among the head, arms and legs. So, the wet status of diaper should be a comparison of diaper temperature in the similar body posture.

The air conditioning module 111 is configured to:
(1) measure ambient temperature near the baby in the fields of view of the CMOS video camera and the thermographic video camera;
(2) control the IR transmitter to send control signal to an air conditioner to adjust control temperature of the air conditioner if the ambient temperature measured in (1) exceeds or falls below a predetermined range.

In real life, some air conditioners are inaccurate in terms of temperature control. As a result, the room temperature or specially the temperature of baby crib is not a comfortable setting for baby. In the present invention, when the air conditioning module 111 detects that the difference between body temperature and room temperature is too high, it can control the room temperature by controlling the air conditioner via an IR transmitter 9 coupled to the microprocessor 1. If the room temperature is higher than comfortable temperature, the air conditioning module 111 will decrease the target temperature of the air conditioner. If the room temperature is lower than comfortable temperature, the air conditioning module 111 will increase the target temperature of the air conditioner. In most cases, the air conditioner will control condenser operational time by detecting the room temperature with reference to outdoor environment. When the outdoor environment is very hot, the resultant room temperature is high too. When the outdoor environment is very cold, the resultant room temperature is low too. In contrast, the air conditioner will not sense the human body temperature in its operation. Therefore, we may feel discomfort. As the present invention can detect the body temperature and room temperature with an accuracy of up to ±0.2° Celsius, it is possible to provide a comfortable environment to the baby no matter how the air conditioner works. The methods and processes by which the IR transmitter 9 sends control signal to an air conditioner is well known in the prior art and are not detailed herein.

The baby growth rate module 112 is configured to:
(1) obtain positions of head and limbs of the baby in the field of view of the CMOS video camera from the motion detection module;
(2) determine a baby length by measuring distance between top of head to toes if the posture determined by the motion detection module is a straight posture;
(3) calculate actual baby length based on the baby length determined in (2) and a scale factor which is based on either dimension of object nearby the baby, manual measurement of the actual baby length in regular basis, or proximity distance between the baby and the multi-purpose video monitoring camera; specifically:
(3.1) perform object recognition on input obtained from the CMOS camera to identify an object positioned near the baby;
(3.2) measure dimension of the object identified in (3.1);
(3.3) recall actual dimension of the object identified in (3.2) from a database which stores actual dimensions of objects;
(3.4) calculate actual baby length based on the baby length determined in (2), the dimension measured in (3.2) and the actual dimension recalled in (3.3);
(4) build a history of the actual baby length calculated in (3).

In operation, during motion detection, there are some situations when the head and four limbs are clearly visible to the CMOS video camera 2. The baby growth rate module 112 can measure length of baby from top of head to the toss and build a history of baby growth rate.

In most cases, parent will put some toys or dolls inside the crib for baby to entertain during alone time. These objects are fixed in dimension after they appear in the crib. In the worst case, the crib itself is the last object we can use as reference. When the baby growth rate module 112 uses object recognition to find out any new objects in the crib, a snapshot of the object will be sent to parent for requesting parent to enter the dimension of the object. For crib, the dimension of mattress can be used for this purpose. The provided dimension is used as a reference to estimate the baby length. When the baby is clearly visible to the CMOS video camera 2, the measurement will be done on the baby length and the dimension of closest object. The ratio between actual dimension of the object and the measured dimension of the object will be used to scale the measured baby length to the actual baby length.

There is another way to obtain the actual baby length by using the video data. A proximity sensor 10 which is coupled to the microprocessor 1 is used to measure the distance between the baby and the CMOS video camera 2. Then, the scale factor is created to figure out the actual length from the measured length and the proximity distance. For example, in proximity distance of 1 meter, the actual length is equal to 10 times of measured length. The closer the proximity distance is, the smaller the scaling factor is.

The last method is to request parent measuring the actual baby length in regular basis for calibration. In the motion detection process, the common position and posture to have clearly visibility on head and four limbs can be determined. The snapshot of this situation will be sent to parent for manual measurement on the baby length. The input from parent and the measured baby length through the CMOS video camera 2 will act a reference in near future to automatically calculate the actual baby length. The reason for regular manual measurement is to minimize the error in scaling the measured length to actual length. Then, the growth rate history will be more realistic.

An exemplary operation process of the present embodiment is detailed as follows:

When the multi-purpose video monitoring camera is switched on, the baby presence detection module 101 will scan any human face including adult and baby. If baby presence is confirmed, the check-in status will be updated as check-in. At this time, the baby presence detection module 101 will capture high resolution of the baby face for facial analysis since it is the moment when the baby head is closest to the CMOS video camera 2.

After check-in, data from the CMOS video camera 2 and the thermographic video camera 3 is continuously sent to the motion detection module 103 to determine if the baby is idle without significant movement for a predetermined period of time.

If the motion detection module determined that the baby is idle without significant movement for a predetermined period of time, the breathing detection module 104 is triggered to calculate the breathing rate of the baby. If the current position of the head of the baby is available from the motion detection module 103, the current position of the head of the baby will be used; otherwise, the last head position found in the motion history in the motion detection module 103 is used. If the breathing rate is less than 10 times per minute, the suffocation detection module 108 is activated.

When the baby is in large motion activity (i.e. the motion detection module 103 does not determine that the baby is idle without significant movement for a predetermined period of time), the breathing detection module 104 and the suffocation detection module 108 are deactivated.

No matter if the baby is active or not, the temperature measurement module 109, the air conditioning module 111 and the urination and defecation detection module 110 are in-place when the baby is present in the monitoring area.

When the baby is not present in the monitoring area, the baby growth rate module 112 is activated to calculate actual baby length and build a history of the actual baby length.

Before and after check-in and check-out, any adult faces captured by the baby presence detection module 101 could be used to determine when and who take in/take away the baby from the monitoring area. The face recognition applied to adult face could generate a database for common person such as baby's mother or helper who will appear in the monitoring area. It is assumed that the person who takes in the baby is a trusted person. So, this person is able to take the baby away from the monitoring area without any special attention. When a stranger is found to take away the baby, the present invention can alert the parent for this situation through the warning module 102.

The embodiment described above is a preferred embodiment of the present invention. It is understood that the present invention should not be limited to the embodiment as described. Any changes, modifications, replacements, combinations and simplification without deviating from the essence and principle of the present invention should be considered alternative configurations that are equally effective and should also fall within the scope of protection of the present invention.

What is claimed is:

1. A multi-purpose video monitoring camera comprising:
a microprocessor;
a CMOS video camera operably coupled to the microprocessor;
a thermographic video camera operably coupled to the microprocessor and aligned with the CMOS video camera so that the thermographic video camera and the CMOS video camera have overlapping fields of view;
a display unit operably coupled to the microprocessor;
the microprocessor comprises a breathing detection module for calculating a breathing rate of a baby, and a suffocation detection module which is activated after the breathing rate of the baby determined by the breathing detection module falls below a predetermined threshold;

the suffocation detection module is configured to:
(1) obtain input from the CMOS video camera and the thermographic video camera;
(2) detect a position of a lead of the baby in the field of view of the thermographic video camera and perform face recognition on the input obtained in (1) to determine if a forehead of the baby is present in the field of view of the CMOS video camera;
(3) if output from (2) indicates that the forehead of the baby is not present, control a warning module of the microprocessor to output a warning signal;
(4) if output from (2) indicates that the forehead of the baby is present, perform face recognition on the input obtained in (1) to determine if a nose and a mouth of the baby is present in the field of view of the CMOS video camera;
(5) if output from (4) indicates that the nose and/or the mouth of the baby is not present, control the warning module to output a warning signal.

2. The multi-purpose video monitoring camera as in claim 1, wherein the suffocation detection module reduces a false alarm by further configured to:
(6) if output from (4) indicates that the nose and/or the mouth of the baby is not present, determine head position of the baby from the input obtained in (1), measure head length and head width of the baby, and determine if a ratio of the head length to the head width deviates from a predetermined ratio;
(7) if output from (6) indicates that the ratio of the head length to the head width deviates from a predetermined ratio, control the warning module to output a warning signal.

3. The multi-purpose video monitoring camera as in claim 1, wherein the microprocessor further comprises a motion detection module which is configured to determine whether the baby is idle for a predetermined period of time, and one of more of a hot air exhalation module, a chest movement module and a breathing sound detection module; the breathing detection module is configured to calculate the breathing rate of the baby based on outputs from one or more of the hot air exhalation module, the chest movement module and the breathing sound detection module if the motion detection module determines that the baby is idle for a predetermined period of time.

4. The multi-purpose video monitoring camera as in claim 3, wherein the hot air exhalation detection module is configured to:
(1) obtain position of head of the baby in the fields of view of the CMOS video camera and the thermographic video camera;
(2) detect position of the nose and the mouth of the baby in the fields of view of the CMOS video camera and the thermographic video camera from the position of head of the baby obtained in (1);
(3) detect temperature variation pattern in the position of the nose and the mouth of the baby in the fields of view of the thermographic video camera detected in (2);
(4) calculate a first breathing rate of the baby based on output obtained in (3).

5. The multi-purpose video monitoring camera as in claim 3, wherein the chest movement detection module is configured to:
(1) obtain positions of head and limbs of the baby in the fields of view of the CMOS video camera and the thermographic video camera;
(2) estimate position of chest based on positions of head and limbs of the baby obtained in (1);

(3) detect pixel-wise spatial variation of the position of chest from frame to frame and convert the spatial variation into frequency domain;
(4) determine the largest magnitude in the frequency domain;
(5) calculate a second breathing rate of the baby based on output obtained in (4).

6. The multi-purpose video monitoring camera as in claim 3, further comprising a mic array operably coupled to the microprocessor; the breathing sound detection module is configured to:
(1) obtain input from the mic array;
(2) perform beamforming on the input obtained in (1) to focus on sound produced near the mouth and the nose of the baby;
(3) detect sound pressure level of output from (2);
(4) build a history of the sound pressure level detected in (3);
(5) calculate a third breathing rate of the baby by counting number of cycles per minute between sound pressure level higher than a predetermined threshold value and sound pressure level lower than a predetermined threshold value from the history of sound pressure level in (4).

7. The multi-purpose video monitoring camera as in any one of claims 3-6, wherein the breathing detection module is configured to determine the breathing rate of the baby by comparing the first breathing rate obtained from the hot air exhalation detection module, the second breathing rate obtained from the chest movement detection module and the third breathing rate obtained from the breathing sound detection module and selecting a maximum amongst the first, second and third breathing rates.

8. The multi-purpose video monitoring camera as in claim 7, wherein the microprocessor further comprises a baby presence detection module which is configured to:
(1) obtain input from the CMOS video camera;
(2) perform face recognition on the input obtained in (1) to determine if a baby is present in the field of view of the CMOS video camera;
(3) if it is determined from (2) that a baby is present in the field of view of the CMOS video camera, confirm baby presence;
(4) if it is determined from (2) that a baby is not present in the field of view of the CMOS video camera, obtain input from the thermographic video camera to identify a human head region in the field of view of the thermographic video camera;
(5) perform face recognition on the input obtained in (1) at a region corresponding to the human head region in the field of view of the thermographic video camera to determine if a baby is present in the field of view of the CMOS video camera;
(6) if it is determined from (5) that a baby is present in the field of view of the CMOS video camera, confirm baby presence;
(7) if it is determined from (5) that a baby is not present in the field of view of the CMOS video camera, confirm baby absence;
(8) if baby presence is confirmed, update check-in/check-out status as check-in;
(9) if baby absence is confirmed, update check-in/check-out status as check-out.

9. The multi-purpose video monitoring camera as in claim 8, wherein the motion detection module is activated after the baby presence detection module updates check-in/check-out status as check-in and is configured to:

(1) obtain input from the CMOS video camera and the thermographic video camera;
(2) detect positions of head and limbs of the baby in the fields of view of the CMOS video camera and the thermographic video camera from the input obtained in (1);
(3) determine posture of the baby by measuring height levels of the detected head and limbs, curvature and orientation of the detected limbs, and separation among the detected head and limbs;
(4) determine motion of the baby based on frame by frame analysis of the posture determined in (3) over a period of time;
(5) build a history of the motion determined in (4);
(6) determine whether the baby is idle for a predetermined period of time from the history built in (5).

10. The multi-purpose video monitoring camera as in claim 1, wherein the warning signals output from the warning module of the microprocessor are in form of warning messages displayed on the display unit; the multi-purpose video monitoring camera is wirelessly connected to an external mobile device which is installed with an app for receiving and outputting the warning messages output from the microprocessor.

11. The multi-purpose video monitoring camera as in claim 1, wherein the microprocessor further comprises a temperature measurement module configured to:
(1) determine a body temperature of the baby by selecting the highest temperature in the field of view of the thermographic video camera;
(2) build a history of the body temperature obtained in (1);
(3) control the warning module to output a warning signal if the body temperature in the history exceeds a predetermined level longer than a predetermined period of time.

12. The multi-purpose video monitoring camera as in claim 11, further comprising a thermistor for calibrating input of the thermographic video camera by compensating difference between ambient temperature and operation temperature of the multi-purpose video monitoring camera.

13. The multi-purpose video monitoring camera as in claim 1, wherein the microprocessor further comprises a urination and defecation detection module configured to:
(1) obtain positions of legs of the baby in the fields of view of the CMOS video camera and the thermographic video camera;
(2) estimate position of diaper based on positions of legs of the baby obtained in (1);
(3) detect and build a history of temperature at the position of diaper estimated in (2);
(4) control the warning module to output a warning signal if the temperature in the history built in (3) indicates a rapid increase follows by a gradual decrease.

14. The multi-purpose video monitoring camera as in claim 1, further comprising an IR transmitter operably coupled to the microprocessor, the microprocessor further comprises an air conditioning module configured to:
(1) measure ambient temperature near the baby in the fields of view of the CMOS video camera and the thermographic video camera;
(2) control the IR transmitter to send control signal to an air conditioner to adjust control temperature of the air conditioner if the ambient temperature measured in (1) exceeds or falls below a predetermined range.

15. The multi-purpose video monitoring camera as in claim 9, further comprising a proximity sensor operably coupled to the microprocessor; the microprocessor further comprises a baby growth rate module configured to:
- (1) obtain positions of head and limbs of the baby in the field of view of the CMOS video camera from the motion detection module;
- (2) determine a baby length by measuring distance between top of head to toes if the posture determined by the motion detection module is a straight posture;
- (3) calculate actual baby length based on the baby length determined in (2) and a scale factor which is based on either dimension of object nearby the baby, manual measurement of the actual baby length in regular basis, or proximity distance between the baby and the multi-purpose video monitoring camera;
- (4) build a history of the actual baby length calculated in (3).

16. The multi-purpose video monitoring camera as in claim 15, wherein the baby growth rate module is further configured to:
- (3.1) perform object recognition on input obtained from the CMOS camera to identify an object positioned near the baby;
- (3.2) measure dimension of the object identified in (3.1);
- (3.3) recall actual dimension of the object identified in (3.2) from a database which stores actual dimensions of objects;
- (3.4) calculate actual baby length based on the baby length determined in (2), the dimension measured in (3.2) and the actual dimension recalled in (3.3).

17. The multi-purpose video monitoring camera as in claim 1, further comprising a rotate-pan-tilt mount operably coupled to the microprocessor and controlled by the microprocessor to adjust the CMOS video camera and the thermographic video camera such that the baby is always in center of the fields of view of the CMOS video camera and the thermographic video camera.

18. The multi-purpose video monitoring camera as in claim 1, wherein the CMOS video camera is a low lux CMOS video camera.

19. The multi-purpose video monitoring camera as in claim 1, wherein the thermographic video camera has a resolution of 32×32 pixels which can measure human body temperature with an accuracy of up to ±0.2° C. at a distance of 1.5 meters from a human body.

* * * * *